United States Patent [19]
Hummel et al.

[11] Patent Number: 5,551,426
[45] Date of Patent: Sep. 3, 1996

[54] INTRACARDIAC ABLATION AND MAPPING CATHETER

[76] Inventors: John D. Hummel, 3437 Burbank, Ann Arbor, Mich. 48105; Ronald D. Berger, 3101 Northbrook Rd., Baltimore, Md. 21208

[21] Appl. No.: 92,438

[22] Filed: Jul. 14, 1993

[51] Int. Cl.⁶ .............................. A61B 5/04; A61N 1/05
[52] U.S. Cl. ............................................ 128/642; 607/122
[58] Field of Search ........................... 128/642; 607/119, 607/122, 123, 125, 126, 128

[56] References Cited

U.S. PATENT DOCUMENTS

| | | |
|---|---|---|
| Re. 32,204 | 7/1986 | Halvorsen . |
| 3,865,118 | 2/1975 | Bures ........................... 607/123 |
| 4,112,952 | 9/1978 | Thomas et al. ................. 607/128 |
| 4,522,212 | 6/1985 | Gelinas et al. . |
| 4,699,147 | 10/1987 | Chilson et al. . |
| 4,793,351 | 12/1988 | Landman et al. . |
| 4,846,791 | 6/1989 | Hattler et al. . |
| 4,894,057 | 1/1990 | Howes . |
| 4,940,064 | 7/1990 | Desai . |
| 4,966,597 | 10/1990 | Cosman . |
| 5,025,786 | 6/1991 | Siegel . |
| 5,122,115 | 6/1992 | Marks . |
| 5,156,151 | 10/1992 | Imran . |
| 5,237,996 | 8/1993 | Waldman et al. ................. 128/642 |
| 5,282,845 | 2/1994 | Bush et al. ................. 607/128 |
| 5,327,889 | 7/1994 | Imran ........................... 128/642 |

Primary Examiner—Lee S. Cohen
Attorney, Agent, or Firm—Henderson & Sturm

[57] ABSTRACT

An assembly of preformed curved enamel-coated ablative tipped endocardial electrodes are housed inside an outer sheath in a preformed geometric arrangement for insertion into heart chambers and application onto the endocardial surface of the heart. The position of the electrodes relative to each other is predetermined by their arrangement on a Teflon bushing which serves as a platform anchored on the end of an inner sheath. The inner sheath is moveable relative to the outer sheath thus allowing graded exposure of the electrodes controlling movement toward the apical and lateral walls of the chamber. Ablative energy is delivered through the 8 mm J-tipped electrode to destroy the arrhythmia focus or reentrant circuit.

22 Claims, 5 Drawing Sheets

INTRACARDIAC ABLATION AND MAPPING CATHETER

FIELD OF THE INVENTION

The present invention relates to intracardiac ablation catheters, particularly intracardiac ablation catheters, and intracardiac mapping catheters, and their uses, including endocardial ablation and mapping.

DISCUSSION OF BACKGROUND INFORMATION

With the recent advances in radio frequency ablation, cardiac electrophysiologists have been able to effectively treat a variety of ventricular and supraventricular arrhythmias with catheter techniques. Most catheters currently in use employ a single ablation tip that can be steered with one or two degrees of freedom. Although some centers have been able to achieve a level of proficiency with these devices that limits procedure time to 2-3 hours, many individual cases still require five or more hours and, often, a repeat visit with more radiation exposure. The majority of this time would be eliminated if one rapidly locates the tachycardia focus, circuit or pathway.

Examples of endocardial apparatus and devices, include those described in U.S. Pat. No. 4,522,212, Gelinas et. al.; U.S. Pat. No. 4,699,147, Chilson et. al.; U.S. Pat. No. 4,793,351, Landman et. al.; U.S. Pat. No. 4,846,791; Hattler et. al.; U.S. Pat. No. 4,894,057, Howes; U.S. Pat. No. 4,940,064, Desai; U.S. Pat. No. 4,966,597, Cosman; U.S. Pat. No. 5,025,786, Siegel; U.S. Pat. No. 5,122,115, Marks; U.S. Pat. No. 5,156,151, IMRAN; and U.S. Pat. No. Re.32,204, Halvorsen.

U.S. Pat. No. 5,156,151, IMRAN, is directed to an endocardial mapping and/or ablation system that includes a plurality of longitudinally and radially spaced apart electrodes that are disclosed as being useful in performing endocardial mapping accurately and rapidly.

The intracardiac ablation catheter of the present invention is an improvement over prior art devices, notably the system disclosed in U.S. Pat. No. 5,156,151, the advantages of which will appear from the following description in which the preferred embodiment is set forth in detail in conjunction with the accompanying drawings.

SUMMARY OF THE INVENTION

The present invention is directed to an intracardiac catheter, preferred embodiment of intracardiac catheter of the present invention is suitable for use as an intracardiac ablation catheter. The most preferred embodiment of the intracardiac catheter of the present invention is particularly suitable for use as an intracardiac ablation and mapping catheter.

Among the advantages of the intracardiac catheter of the present invention is its simplicity of design and ease of use.

The intracardiac catheter is also advantageous in that vascular complications are avoided or minimized during its use. Although not wishing to be bound by any particular theory, it is believed that such advantage may be attributed, at least in part, to the relatively small size of the intracardiac catheter.

More specifically, the present invention is directed to an intracardiac catheter including an assembly of preformed curved insulated ablative tipped endocardial electrodes that are housed inside an outer sheath in a preformed geometric arrangement for insertion into heart chambers and application onto the endocardial surface of the heart.

The position of the electrodes relative to each other is predetermined by their arrangement on a Teflon bushing which serves as a platform anchored on the end of an inner sheath.

The inner sheath is moveable relative to the outer sheath thus allowing graded exposure of the electrodes controlling movement toward the apical and lateral walls of the chamber.

In a preferred embodiment, the electrodes are provided with a J-tip. The J-tip of the electrodes has been discovered to be particularly advantageous in protecting the endocardial surface from abrasion. The J-tips of the electrodes are particularly advantageous in avoiding perforation of the endocardial surface.

Also, the J-tips of the electrodes, when extended, have been discovered to allow a large surface area of ablation despite the relatively small size of the intracardiac ablation catheter when the electrodes are retracted within the outer sheath.

Among the advantages of the intracardiac catheter of the present invention, particularly the preferred intracardiac ablation and mapping catheter, is that it decreases the time of the endocardial ablation and mapping procedures, and radiation exposure incident thereto; allows accurate detection of single or multiple arrhythmia foci and bypass tracts; and allows accurate rapid mapping of ventricular tachycardia circuits; and allows delivery of ablative energy via the same electrodes as those used for mapping.

With the foregoing in mind, the present invention is directed to an intracardiac ablation and mapping apparatus including a catheter that includes a plurality of longitudinally and radially spaced apart electrodes having a distal curved portion; and preferably a plurality of insulated wires, each of the insulated wires being attached to one of the plurality of longitudinally and radially spaced apart electrodes.

The present invention is also directed to an intracardiac ablation and mapping apparatus, as otherwise described herein, that includes a guidewire in addition to the previously described elements.

The present invention is also directed to an intracardiac ablation and mapping apparatus, as otherwise described herein, that includes a housing for the insulated wires; a bushing movably disposed within the housing and attached to a proximal end of each of the insulated wires; and a plurality of electrical wires extending through the length of the catheter to the bushing, wherein each of the insulated wires penetrates the bushing and is attached to one of the plurality of electrical wires.

The present invention is also directed to the intracardiac ablation and mapping apparatus, as otherwise described herein, that further includes a solder connection for connecting each of the insulated wires to one of the electrical wires, preferably wherein the distal ends of the electrical wires are bound together as a cable having a proximal end exiting the catheter.

The present invention is also directed to the intracardiac ablation and mapping catheter, as otherwise described herein, that preferably also includes at least one member selected from the group consisting of an electrical connection fastened to the proximal end of the cable, an interface module operably connected to the proximal end of the cable, and a chart recorder operably connected to the proximal end of the cable.

The present invention is also directed to the intracardiac ablation and mapping apparatus, as otherwise described herein, wherein the distal curved portion of the electrodes have a reduced caliber and tensile strength relative to the remainder of the electrode, and preferably wherein the electrodes comprise wire of conductive material wound around the distal curved portion of the electrodes.

The present invention is also directed to the intracardiac ablation and mapping apparatus, as otherwise described herein, which also includes an intracatheter channel within the housing.

The present invention is also directed to an intracardiac ablation and mapping apparatus, as otherwise described herein, that includes a locking nut operably connected to the guidewire for maintaining the guidewire to a predetermined degree of extension beyond a distal curved portion of the electrodes, preferably wherein the guidewire comprises an electrode, and/or the curved distal portion of the electrodes includes a J-tip.

The present invention is also directed to an intracardiac ablation and mapping apparatus, as otherwise described herein, wherein at least one of the electrodes is bipolar.

The present invention is also directed to an intracardial method that involves positioning an intracardial catheter, as otherwise described herein, in a ventricular chamber of the heart. For the purpose of the method of the present invention, the intracardial catheter preferably includes a plurality of longitudinally and radially spaced apart electrodes having a distal curved portion; a guidewire comprising an electrode; a plurality of insulated wires, each of the insulated wires being attached to one of the plurality of longitudinally and radially spaced apart electrodes; and an inner sheath and an outer sheath surrounding the distal curved portion of the electrodes.

The present invention is also directed to the intracardial method, as otherwise described herein, that involves advancing the inner sheath of the catheter through the outer sheath; and exposing the distal curved portion of the electrodes and impinging the distal curved portion of the electrode tips against an endocardial wall of the heart.

The present invention is also directed to the intracardial method, as described above, which also includes applying energy from the distal curved portion of the electrode tips to the endocardial wall.

The present invention is also directed to the intracardial method, described above, which also includes taking electrograms measured between the electrode of the guidewire and the electrodes located at multiple circumferential endocardial sites.

The present invention is also directed to the intracardial method, as described above, wherein the electrodes comprise at least one bipolar electrode, which also includes taking bipolar electrograms from between the bipoles of the bipolar electrode.

BRIEF DESCRIPTION OF THE DRAWINGS

Further features, objects, and advantages of the present invention will be more readily apparent from the following more detailed description thereof when taken in conjunction with the following drawings.

DESCRIPTION OF THE INVENTION

The present invention relates to an intracardiac catheter, i.e., a multipolar intracardiac ablation and/or mapping catheter that allows ablation and recording or mapping from several endocardial sites simultaneously. The intracardiac catheter of the present invention, as shown in the drawings, comprises elements as listed below, and as otherwise described in this application:

1. Outer sheath
2. Inner sheath
3. Guidewire or guiding J wire and common electrode for unipolar tines
4. Teflon bushing
5. Electrical wires
6. Preformed steel tines
7. Distal tip of preformed steel time or floppy J-tip with platinum wire wrapping
8. Steel tension wires to control catheter deflection
9. Radio-opaque markers
10. Lock nut for guiding J-wire
11. Electrical cable
12. Multi-conductor plug
13. Deflection controller
14. Platinum wire electrode
15. Steel wire conductor or unipolar tine
16. Enamel coating as insulation on the unipolar tine
17. Preformed steel tine (bipolar tine) covered with insulation
18. Inner steel wire conductor of bipolar tine
19. Outer conductor of bipolar tine
20. Insulator coating between inner and outer conductors of bipolar tine
21. Outer enamel coating as insulation on bipolar tine
22. Platinum ring proximal electrode of bipolar tine
23. Opening in Teflon bushing for enamel-coated steel tines 24. Opening in Teflon bushing for guiding J-wire and common electrode 25. Solder connection between electrical wire and conductor of tine The intracardiac catheter of the present invention is described hereinbelow with respect to the drawings.

Figure 6:
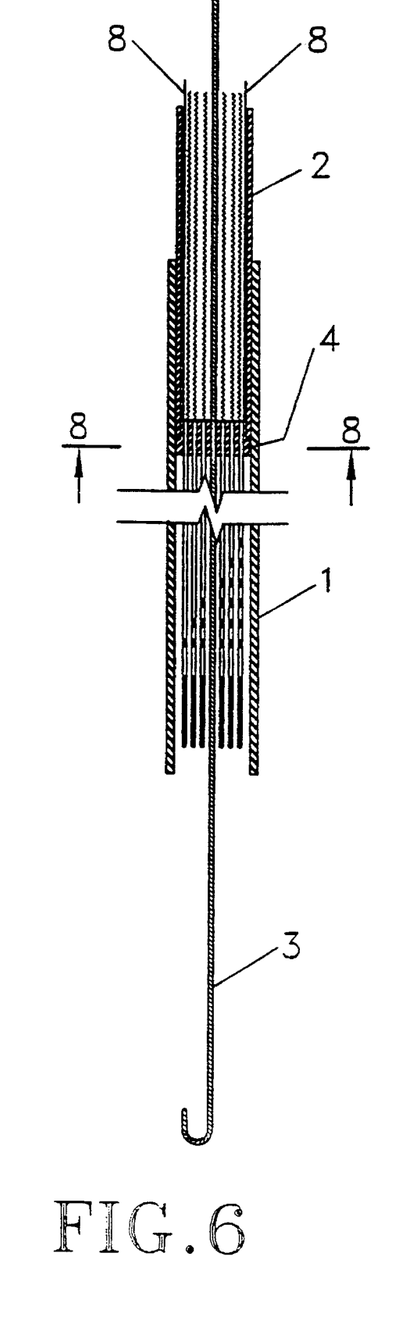
FIG. 6 shows a view of the catheter in the orientation used to place it in the ventricle wherein the inner sheath is retracted so that the distal electrode poles are withdrawn inside the distal end of the outer sheath.
Figure 7:
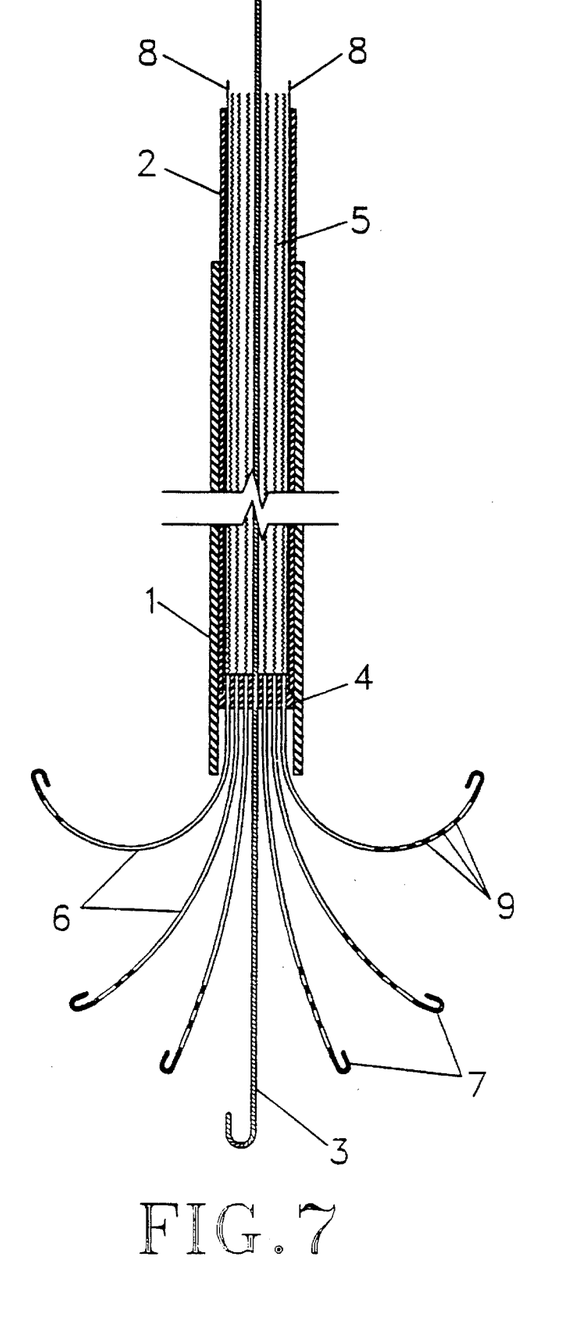
FIG. 7 shows a view of the catheter after the inner sheath has been advanced showing the relative positions of the preformed wires with radiopaque markers and the floppy "J" curve of the distal electrodes.
Figure 8:
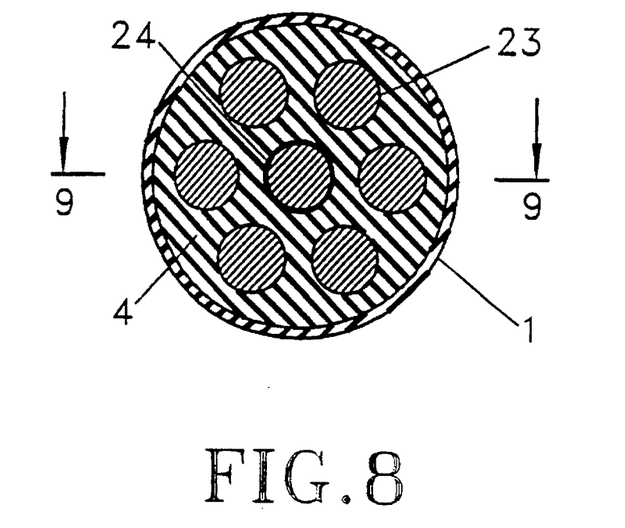
FIG. 8 is a cross section taken across 8—8 of FIG. 6.
Figure 9:
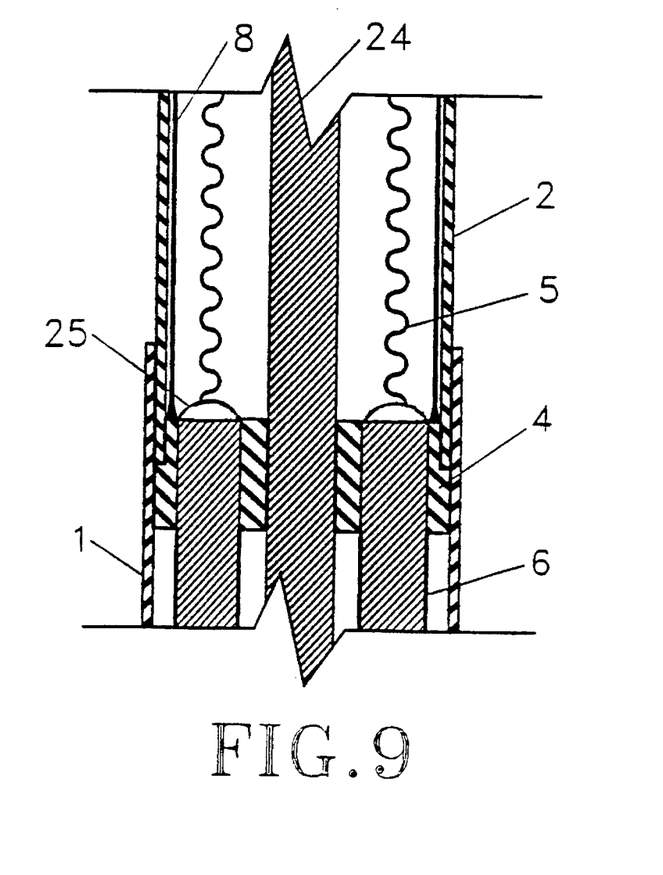
FIG. 9 shows an enlarged section showing the solder connection between electrical wires and the conductor of the electrode.

As shown in FIG. 6, at least one, but preferably a group of a plurality of four to eight precurved wires 6 with J-tips 7, as electrodes, are housed within the end of the core of a nine french hollow catheter C and anchored in Teflon bushing 4, shown in more detail in FIG. 8 and FIG. 9. The wires 6, also referred to herein as electrode wires 6, are preferably preformed wires or tines made of steel, such as stainless steel, and most preferably surgical steel. The wires 6 are at least partially covered with insulation material 16, 21 which is preferably provided by a layer of enamel or an enamel coating over the surface of the wire. The J-tips 7 are preferably 8 mm in length when straightened. As shown in FIGS. 6, 7, 8 and 9, each wire 6 penetrates the Teflon 4 bushing and is attached preferably by solder connections 25, to a malleable insulated, electrical wire 5, which is flexible, and runs the length of the catheter. The electrical wires 5 may also be covered at least partially by insulation material.

Figure 10:
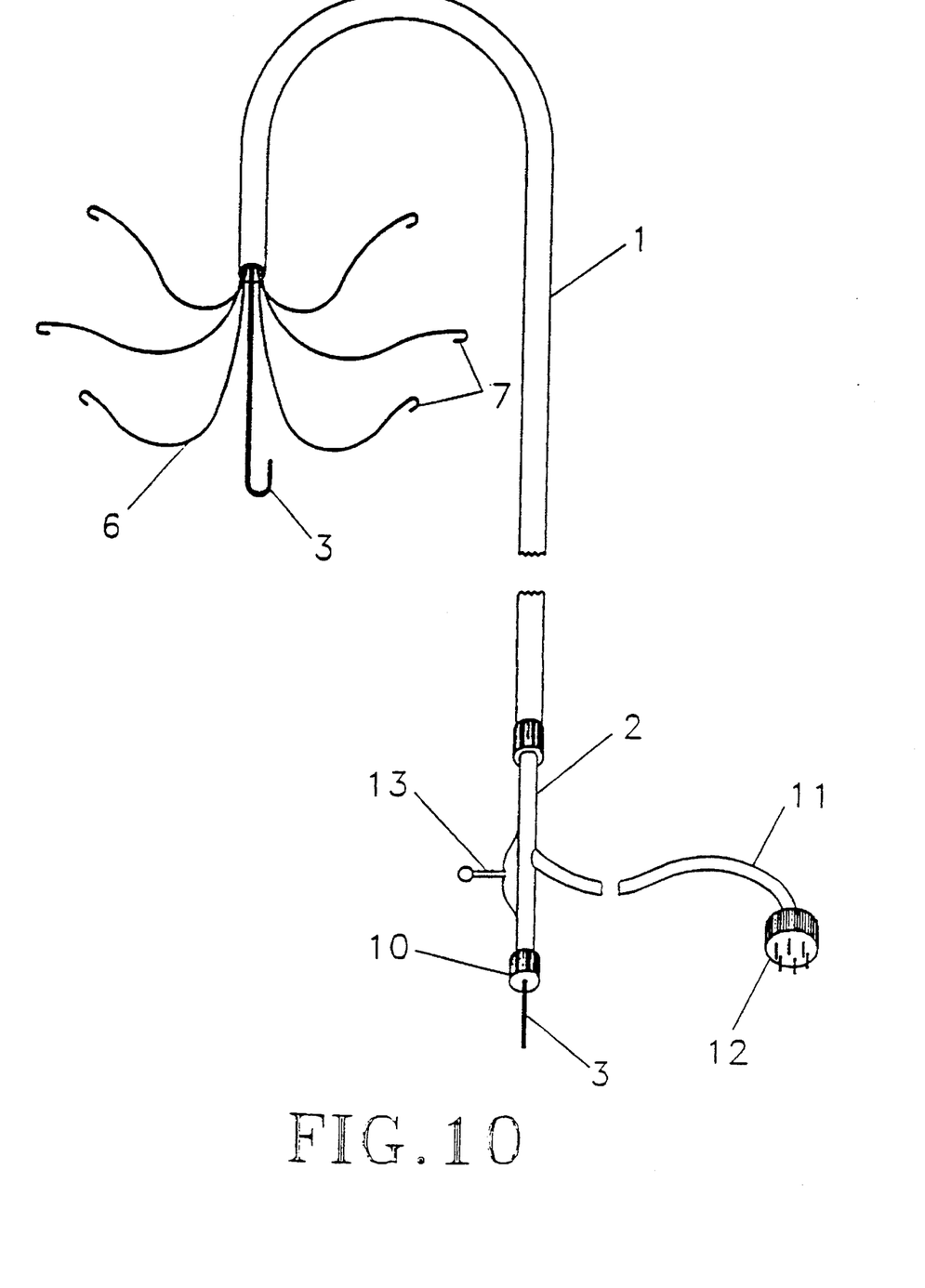
FIG. 10 shows a view of the proximal portion of the catheter, the proximal relationship of the inner and outer sheaths, and how the electrical cable extends from this inner sheath to the multi-connector plug, and the extended appearance of the catheter.

As shown in FIG. 10, these flexible electrical wires 5 are bound together as they exit the catheter to produce an electrical cable 11 which terminates in a multi-connector plug 12, which can then be connected to an electronic device, such as an interface, a computer, or a chart recorder (not shown) and screened for individual signal analysis.

Referring to FIG. 7 and FIG. 10, each electric wire 6 anchored in the Teflon bushing 4 has a preformed distal curve 7, i.e., J-tip 7, that causes the catheter C to impinge upon the nearest lateral or apical endocardial surface depending on the degree of deployment of the tines or deflection of the body of the catheter.

Figure 1:
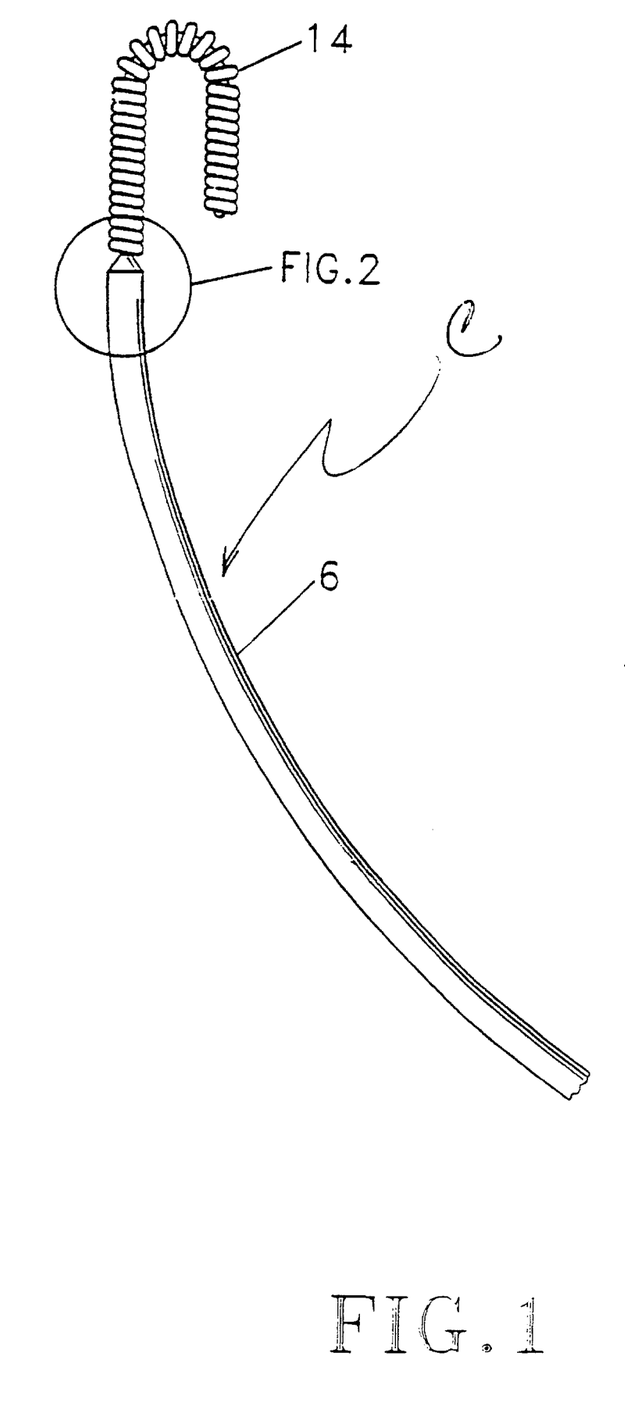
FIG. 1 shows a view of the distal "J" curved electrode, its tapered configuration, and the platinum wrapping around it.
Figure 2:
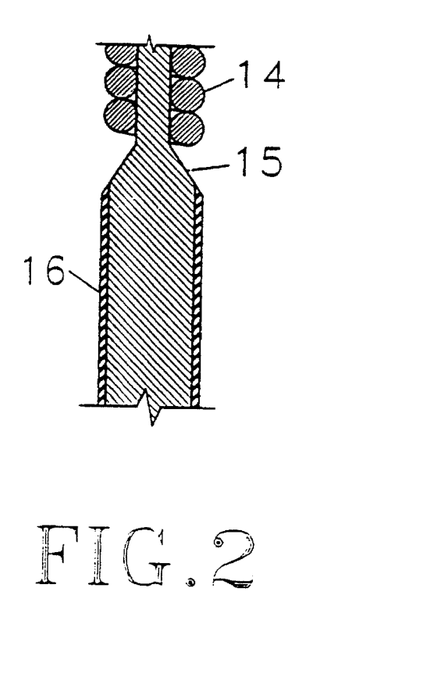
FIG. 2 shows an enlarged section of the electrode of FIG. 1.
Figure 3:
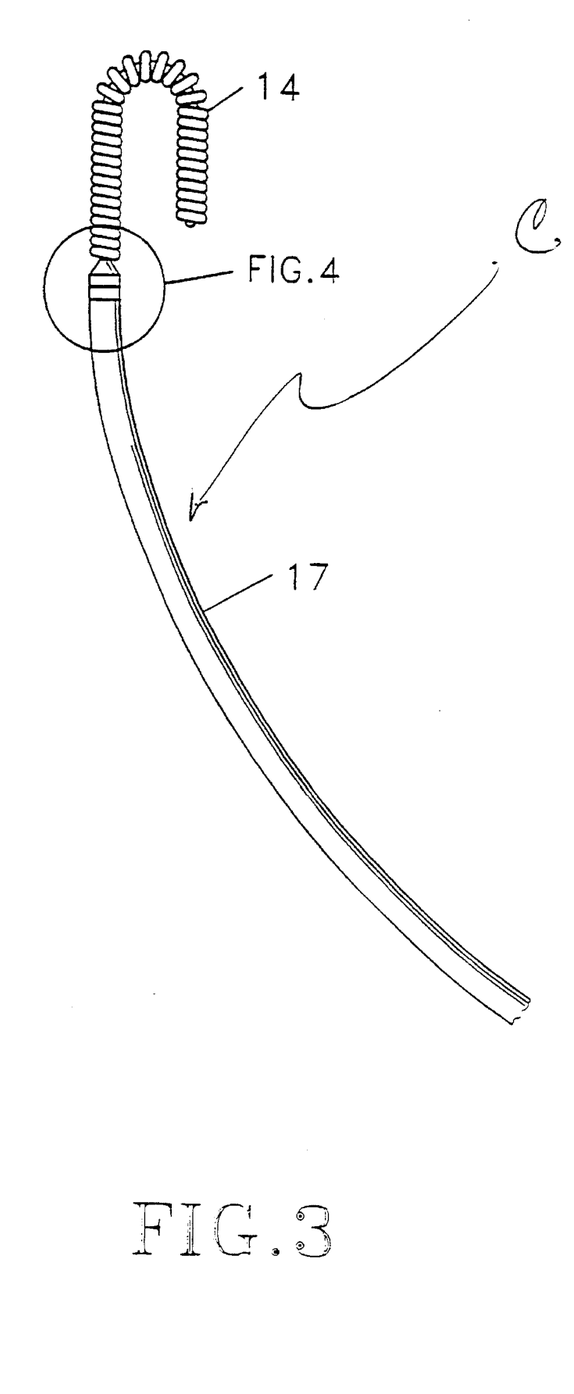
FIG. 3 shown a view of another embodiment of the distal J-curved electrode, its tapered configuration, and the platinum wrapping around it.
Figure 4:
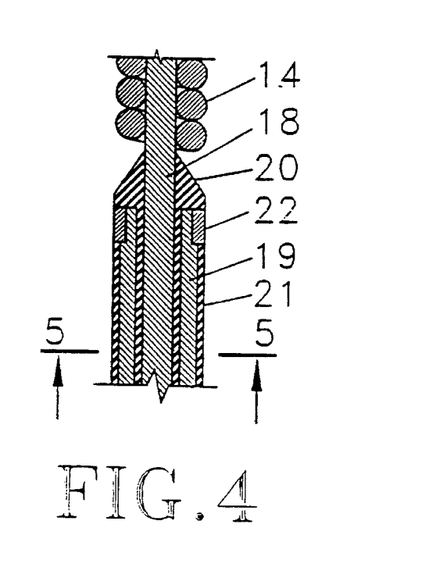
FIG. 4 shows an enlarged section of the electrode of FIG. 3.
Figure 5:
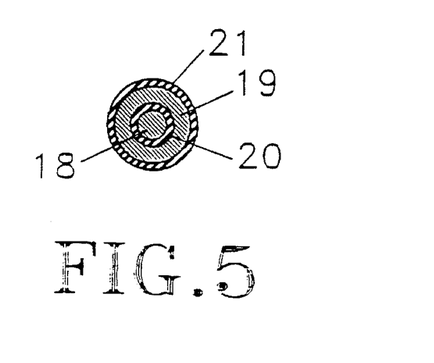
FIG. 5 is a cross section across 5—5 of FIG. 4.

As shown more clearly in FIGS. 1 and 3, and in even more detail in FIGS. 2 and 4, the distal tip 7 of each preformed steel wire 6 has a reduced caliber and tensile strength relative to the remainder of the wire. The reduced caliber and tensile strength of the distal tip of the electrode wire of the intracardiac catheter of the present invention has been discovered to be particularly advantageous in enabling independent flexure of the distal tips to maintain endocardial contact. Referring to FIG. 2, the reduced diameter of the wires 6 is shown as a necked down portion of a steel wire conductor or unipolar tine 15 provided with an insulation layer 16 which is preferably a coating of enamel.

As shown in FIG. 6 and FIG. 7, the intracardiac catheter of the present invention is also provided with steel tension wires 8 as means for controlling deflection of the catheter.

As shown in FIG. 7, the insulated or enamel-coated wires 6 are provided with radio-opaque markers 9.

As shown in FIGS. 1 and 3, wire 14, made of conductive material, such as platinum, is wrapped around the tip to act as its conductive surface. The tip of each preformed steel wire wrapped as shown with platinum wire as an electrode, is used to obtain unipolar or bipolar recordings or mappings, depending on whether the electrode is a unipolar electrode or bipolar electrode, and buffers the endocardium against the stiffness of the proximal wire. The distal tip of the intracardiac catheter of the present invention also functions in the application of ablative, e.g., RF, energy. For purposes of these uses, the intracardiac catheter of the present invention may be referred to as an intracardiac mapping catheter or an intracardiac ablation catheter, respectively.

Referring to FIGS. 6, 7, 8 and 9, an intracatheter channel 24 is provided as an orifice or opening in the Teflon bushing 4 for guiding J-wire 3, also referred to herein as guidewire 3, to allow passage of guidewire 3 to facilitate safe placement of the catheter antegrade into the right atrium or ventricle or retrograde into the left ventricle. This channel allows for intracavitary pressure measurements once the guidewire 3 is removed. The guidewire 3 can also be retained and used as a common electrode. The guidewire 3 is preferably 0.35 mm in diameter.

The distal tip 7 of each tine or preformed wire 6 of the intracardiac ablation catheter of the present invention is relatively floppy due in part to its reduced diameter or caliber and tensile strength relative to the remaining portion of the wire 6, and is also referred to herein as floppy J-tip 7, as well as J-tip 7.

The unique J-tip 7 used for ablation allows resistive heating to occur over a greater area (8 mm folded back on itself) than with the typical 4 mm ablation tip. The J-tip has also been discovered to reduce the risk of cardiac perforation and allows for tight packing when the electrodes and their J-tips are retracted within the outer sheath.

The tapered J-tip of the electrodes allows, when the electrodes are retracted within the housing, for the entire wire 6, including its J-tip, to be straightened so as to easily fit within the housing of the catheter, e.g., defined by the outer sheath. When the wires 6 are moved to extend outside the housing, the J-tip 7 extend radially outwardly to define an area with a diameter substantially larger than the diameter of the housing so as to permit the electrodes to make contact over a larger surface area of the intracardial wall.

In FIG. 3 and 4, another embodiment of the intracardiac ablation catheter is shown similar to that shown in FIG. 1 and FIG. 2, except that the steel tine is shown as a bipolar tine 17, respectively, preferably made of preformed steel, that includes an inner steel wire conductor 18 and an outer conductor 19 with a layer of insulation 20 disposed between the inner conductor 18 and outer conductor 19 of the bipolar tine. The exterior of the bipolar tine 17 is provided with an exterior coating 21 that is preferably an enamel coating. As shown in more detail in FIG. 4, the bipolar tine is provided with a platinum ring 22 proximal to the electrode.

Referring to FIG. 8, Teflon bushing 4 is provided with openings 23 for the insulated or enamel coated steel tines 6 and orifice 24 for the guiding J-wire 3 are shown.

As shown in FIG. 6, 7, 9 and 10, the intracardiac ablation catheter of the present invention includes an outer sheath 1 surrounding an inner sheath 2 for housing the assembly of wires 5, 6, and bushing 4. The relatively independent construction and relationship of the inner sheath 2 and outer sheath 1 allow the operator to remove the inner sheath and replace it with an inner sheath containing differently arranged, longer or shorter electrodes without removing the outer sheath from the ventricle.

The distal peelable or retractable cover or outer sheath 1 allows for ease of placement of the guide wire 3 into the proximal end of the catheter.

A sideport at the proximal end of the catheter allows for administration of intravenous fluids, pharmacologic agents, and flushing of the external sheath, and is shown in FIG. 10 as being equipped with a deflection controller.

As shown in FIG. 10, a locking nut 10 is provided to hold the guidewire 3 to the degree of extension beyond the distal tip of the electrode that is desired.

The intracardiac ablation catheter of the present invention operates in the following manner. The catheter C, as described and illustrated, allows antegrade or retrograde placement into an atrial chamber, or a ventricular chamber. The assembly of preformed curved insulated, enamel-coated ablative tipped endocardial electrodes 14 are housed inside an outer sheath 1 in a preformed geometric arrangement for insertion into heart chambers and application onto the endocardial surface of the heart.

The position of the electrodes 14 relative to each other is predetermined by their arrangement on the Teflon bushing 4 which serves as a platform anchored on the end of an inner sheath. However, each electrode curves independently to make contact with the endocardium.

The inner sheath 2 is moveable relative to the outer sheath 1 thus allowing graded exposure of the electrodes 7 controlling movement toward the apical and lateral walls of the chamber.

Catheter C in FIG. 6 is shown in the orientation used to place it in a heart chamber, e.g., the ventricle, where the inner sheath 12 is retracted so that the distal poles are withdrawn inside the distal end of the outer sheath 1, i.e., the 0.35 mm guide wire 3 is to be placed in the chamber of interest, the catheter is then deflected to the appropriate angle, and the catheter C guided into the chamber over the guidewire 3. Once positioned, the multiple poles 7 can be extended by advancing the inner sheath 2 through the stabilized outer sheath 1 and thus allow impingement of the electrodes 7 against the endocardial wall. FIG. 7, shows the catheter C after the inner sheath 2 has been advanced showing the relative positions of the preformed wires with radiopaque markers 9 and the floppy "J" curve of the distal electrodes 7.

This catheter array allows for simultaneous analysis of unipolar electrograms measured between the guidewire 3 and the electrodes 14 or bipolar electrograms measured between electrodes 14 and 22 located at multiple circumferential endocardial sites. If the signal at a particular pole is consistent with a site vulnerable to radio frequency ablation, such energy may be selectively delivered to that site via the catheter pole. In the case of AV bypass tracts and ventricular tachycardia this allows for rapid identification of the general location of the bypass tract or region of slow conduction, respectively.

Pulling the entire apparatus retrograde from apex to outflow tract and pacing and measuring from the electrodes allows accurate localization of the tract or circuit. When localization is felt to be adequate, radiofrequency or some other suitable energy can be delivered to the pole or poles presumed to be closest to the pathway, focus, circuit, etc. allowing effective ablation of the region. It is also contemplated that the intracardiac ablation catheter be designed so that with individual manipulation of a pole available, repositioning of a pole location and ablation can be undertaken without maneuvering the entire catheter in the case of initial failure. Such an approach eliminates the multiple catheter insertions and manipulations necessary with a single ablative tip catheter and the inherent time and risks associated with such manipulations. In addition, the circumferential placement of the poles creates greater stability of contact between the tip and the endocardium which should decrease the risk of arrhythmia recurrence. As used herein, the functions of mapping and ablation involve retraction, slight rotation and redeployment of the catheter.

Steerability of the catheter is provided by two tension wires 8 that run within the inner sheath from the Teflon bushing at the distal end to the handle at the proximal end. A lever in the handle adjusts the relative tension placed on these wires. The distal portion of the catheter, including the electrode assembly, then deflects toward the side with the wire of greater tension. With the combination of catheter rotation and deflection, 360 degree steerability can be achieved.

It is also contemplated that the intracardiac catheter of the present invention, as otherwise described herein, be constructed so as to have independent suspension of each tine. Such construction would allow for separate and independent manipulation or movement of each tine for separate contact with an area on the intracardial wall.

It will be appreciated to those of ordinary skill in the art that while the present invention has been described herein by reference to particular means, methods, and materials, the scope of the present invention is not limited thereby, and extends to any and all other means. Methods, and materials suitable for practice of the present invention.

What we claim is:

1. An intracardiac ablation and mapping apparatus comprising:
   a catheter comprising:
   a housing;
   a plurality of radially spaced apart insulated electrodes for mapping and ablating having a distal curved portion, said distal curved portion being operatively deployable from said housing;
   a plurality of insulated wires, each of said insulated wires being attached to one of said plurality of radially spaced apart electrodes for mapping and ablating, and a guidewire, said plurality of insulated wires and said guidewire being at least partially disposed in said housing; and
   a bushing movably disposed within said housing and attached to a proximal end of each of said insulated wires.

2. The intracardiac ablation and mapping apparatus of claim 1, wherein said catheter comprises a plurality of electrical wires extending through the length of said catheter to said bushing and structure for connecting said plurality of electrical wires connected to said insulated wires.

3. The intracardiac ablation and mapping apparatus of claim 2, wherein each of said insulated wires penetrates said bushing and is attached to one of said plurality of electrical wires.

4. The intracardiac ablation and mapping apparatus of claim 3, wherein said structure for connecting comprises a solder connection connecting each of said insulated wires to one of said electrical wires.

5. The intracardiac ablation and mapping apparatus of claim 4, wherein distal ends of said electrical wires are bound together as a cable having a proximal end exiting said catheter.

6. The intracardiac ablation and mapping apparatus of claim 5, further comprising an electrical connection fastened to the proximal end of said cable.

7. The intracardiac ablation and mapping apparatus of claim 5, further comprising an interface module operably connected to the proximal end of said cable.

8. The intracardiac ablation and mapping apparatus of claim 5, further comprising a chart recorder operably connected to the proximal end of said cable.

9. The intracardiac ablation and mapping apparatus of claim 3, comprising an intracatheter channel within said housing.

10. The intracardiac ablation and mapping apparatus of claim 3, comprising a locking nut operably connected to said guidewire for maintaining the guidewire to a predetermined degree of extension beyond a distal curved portion of the electrodes for mapping and ablating.

11. The intracardiac ablation and mapping apparatus of claim 10, wherein said guidewire comprises an electrode.

12. The intracardiac ablation and mapping apparatus of claim 1, wherein said distal curved portion of the electrodes for mapping and ablating have a reduced caliber and tensile strength relative to the remainder of said electrode.

13. The intracardiac ablation and mapping apparatus of claim 12, wherein said electrodes for mapping and ablating, comprise wire of conductive material wound around said distal curved portion of said electrodes for mapping and ablating.

14. The intracardiac ablation and mapping apparatus of claim 12, wherein said distal curved portion of the electrodes for mapping and ablating comprise a J-tip.

15. The intracardiac ablation and mapping apparatus of claim 14, wherein at least one of said electrodes for mapping and ablating comprises a bipolar electrode.

16. An intracardial method comprising:
   positioning an intracardial catheter in a ventricular chamber of a heart, said intracardial catheter comprising:
      a housing;
      a plurality of radially spaced apart electrodes for mapping and ablating having a distal curved portion;
      a guidewire comprising an electrode;
      a plurality of insulated wires, each of said insulated wires being attached to one of said plurality of radially spaced apart electrodes for mapping and ablating;
      an inner sheath and an outer sheath surrounding said distal curved portion of said electrodes;
   advancing the inner sheath of said catheter through said outer sheath; and
   exposing said distal curved portion of said electrodes for mapping and ablating and impinging said distal curved portion of said electrodes for mapping and ablating against an endocardial wall of the heart.

17. The intracardial method of claim 16, further comprising taking electrograms measured between said electrode of said guidewire and said electrodes located at multiple circumferential endocardial sites.

18. The intracardial method of claim 16, wherein said electrodes comprise at least one bipolar electrode, and said method further comprises taking bipolar electrograms from between bipoles of said at least one bipolar electrode.

19. The intracardial method of claim 16, further comprising applying energy from the distal curved portion of said electrodes for mapping and ablating to the endocardial wall.

20. An intracardiac ablation and mapping apparatus comprising:
   a catheter comprising:
      a housing;
      a plurality of radially spaced apart electrodes having a distal curved portion, said plurality of radially spaced apart electrodes being operably associated with said housing;
      a plurality of insulated wires, each of said insulated wires being attached to one of said plurality of radially spaced apart electrodes, and
      a guidewire, wherein said plurality of insulated wires and said guidewire are at least partially disposed in said housing; and
      a bushing disposed within said housing and attached to a proximal end of each of said insulated wires.

21. An intracardiac ablation and mapping apparatus comprising:
   a catheter comprising:
      a housing; and
      a plurality of radially spaced apart electrodes having a distal curved portion, said plurality of radially spaced apart electrodes being operably deployable from said housing;
      a plurality of insulated wires, each of said insulated wires being attached to one of said plurality of radially spaced apart electrodes, wherein said plurality of insulated wires are at least partially disposed in said housing, and said distal curved portion of the electrodes have a reduced caliber and tensile strength relative to the remainder of said electrode.

22. An intracardial method comprising:
   positioning an intracardial catheter in a ventricular chamber of a heart, said intracardial catheter comprising:
      a housing;
      a plurality of radially spaced apart electrodes having a distal curved portion;
      a guidewire comprising an electrode;
      a plurality of insulated wires, each of said insulated wires being attached to one of said plurality of radially spaced apart electrodes;
      an inner sheath and an outer sheath surrounding said distal curved portion of said electrodes, wherein said plurality of insulated wires and said guidewire are at least partially disposed in said housing;
   advancing the inner sheath of said catheter through said outer sheath;
   exposing said distal curved portion of said electrodes and impinging said distal curved portion of said electrodes against an endocardial wall of the heart; and
   taking electrograms measured between said electrode of said guidewire and said electrodes located at multiple circumferential endocardial sites.

* * * * *